(12) United States Patent
Ju et al.

(10) Patent No.: US 11,399,960 B2
(45) Date of Patent: Aug. 2, 2022

(54) METHOD TO TREAT OSTEOPOROTIC VERTEBRAL BODY

(71) Applicant: JOY MEDICAL DEVICES CORPORATION, Kaohsiung (TW)

(72) Inventors: Chien-Ping Ju, Kansas City, MO (US); Jiin-Huey Chern Lin, Winnetka, IL (US)

(73) Assignee: JOY MEDICAL DEVICES CORPORATION, Kaohsiung (TW)

( * ) Notice: Subject to any disclaimer, the term of this patent is extended or adjusted under 35 U.S.C. 154(b) by 409 days.

(21) Appl. No.: 16/423,259

(22) Filed: May 28, 2019

(65) Prior Publication Data

US 2020/0376161 A1 Dec. 3, 2020

(51) Int. Cl.

| | |
|---|---|
| *A61F 2/46* | (2006.01) |
| *A61L 27/36* | (2006.01) |
| *A61B 17/88* | (2006.01) |
| *A61F 2/44* | (2006.01) |
| *A61L 27/58* | (2006.01) |

(52) U.S. Cl.
CPC ........ *A61F 2/4601* (2013.01); *A61B 17/8802* (2013.01); *A61L 27/3658* (2013.01); *A61F 2002/444* (2013.01); *A61L 27/58* (2013.01)

(58) Field of Classification Search
CPC .................................................. A61F 2/4601
See application file for complete search history.

(56) References Cited

U.S. PATENT DOCUMENTS

| | | | |
|---|---|---|---|
| 6,248,110 B1 * | 6/2001 | Reiley ................ | A61B 17/8816 606/93 |
| 6,852,095 B1 * | 2/2005 | Ray .................... | A61B 17/7097 604/93.01 |

* cited by examiner

*Primary Examiner* — Andrew Yang

(74) *Attorney, Agent, or Firm* — Bacon & Thomas, PLLC

(57) ABSTRACT

A percutaneous minimally-invasive procedure to prevent a potential fracture in an osteoporotic vertebra of an osteoporotic patient who has no history of vertebral fracture is provided by minimally-invasively injecting a non-dispersive, biocompatible and resorbable calcium-based cement paste into the osteoporotic vertebral body.

1 Claim, No Drawings

METHOD TO TREAT OSTEOPOROTIC VERTEBRAL BODY

FIELD OF THE INVENTION

The present invention is related to a minimally invasive method to prevent a potential fracture in an osteoporotic vertebra of an osteoporotic patient who has no history of vertebral fracture.

BACKGROUND OF THE INVENTION

Osteoporosis has been a major worldwide public health issue. It was estimated that the number of people aged 60 or over in the world was about 960 million in 2017. This number was projected to be 1.4 billion in 2030 and 2.1 billion in 2050. Rather than directly causing pain or disability in itself, osteoporosis weakens the skeletal structure and increases the risk of fracture, most notably involving vertebral body, hip, forearm and femur. It was reported that 40% in women and 15% in men older than 50 might suffer from one of such osteoporosis-related fractures. Tens of billion US dollars were expected to spend annually on osteoporotic fractures each in the U.S., EU and China, which would become a large economic burden in the near future.

The incidence and severity of osteoporotic vertebral compression fracture (OVCF) have been steadily increasing over the last decades among elderly patients. In the U.S., approximately 750,000 adults suffer from OVCFs each year (Han et al., 2011), including 27% of men and women older than 65 years of age. OVCF generally occurs due to insufficient anterior vertebral height and causes spinal deformities, reduced pulmonary function, restriction of the abdominal and thoracic contents, impaired mobility, and depression. Moreover, it prolongs hospitalization, affects quality of life, increases morbidity, and inflicts a heavy burden on the society.

The risk of a spine fracture of a patient is directly related to the bone mineral density (BMD) of the patient. Traditional X-rays cannot measure bone density but can identify spine fractures. A number of different types of BMD tests are available. The most commonly-used technique is dual-energy X-ray absorptiometry (DXA). The World Health Organization (WHO) has identified a number of threshold values for osteoporosis. The reference measurement is derived from bone density measurements in a population of healthy young adults, termed "T-score". Osteoporosis is diagnosed when a person's BMD is equal to or more than 2.5 standard deviations below this reference measurement, i.e., the T-score is −2.5 or lower. Osteopenia is diagnosed when the T-score is between −1 and −2.5. To reduce radiation and costs to a patient, Hounsfield units (HU) measured on CT scans using automatic exposure control has also been used to assess BMD. Batawil et al. (2015) examined the correlation between HU from CT scan and BMD from DXA scan. The authors concluded that a HU of 91 can exclude normal bone density, while a HU of 203 can exclude osteoporosis. The results also indicated that mean HU values consistently decreased with increasing decade of life, from 182.8 in the fourth decade to 82.1 in the eighth.

Different approaches are available for the treatment of OVCFs, including standard medical and surgical therapy. The standard medical therapy contains bed rest, analgesia, bracing, external fixation, rehabilitation, and a combination of these treatments. However, there are several limitations in the standard therapy. Long-term bed rest can lead to demineralization and OVCF recurrence. Anti-inflammatory drugs and certain types of analgesics cause intolerable side effects for older patients. Medical management does not reverse kyphotic deformity. On the other hand, surgical treatment involves surgical stabilization via dorsal instrumentation, which is available for patients with OVCFs who are refractory to standard medical therapy (Dickman et al., 1992).

Due to the poor quality of the osteoporotic bone, classical open surgery with metal implants may fail and leads to persistent back pain, neurological symptoms, and limited functions. As minimal invasive spinal surgery techniques evolved, acute painful vertebral compression fractures might be treated through percutaneous procedures termed vertebroplasty or kyphoplasty. These procedures involve inserting large spinal needles into the fractured vertebral body through a channel usually made in the pedicle and injecting methyl methacrylate (PMMA) bone cement into the fractured bone.

Vertebroplasty was introduced by Galibert and Deramend in 1984 in France for treating hemangiomas at the C2 vertebra. Balloon kyphoplasty was first performed in 1998. Unlike vertebroplasty, kyphoplasty aims not only to secure fracture fixation and stabilization, but also to reconstruct the vertebral anatomy and correct the kyphotic spinal deformity. A deflated balloon is inserted into the vertebral body through the pedicle and inflated to restore the height of a collapsed vertebral body and create a cavity inside. The balloon is then deflated and withdrawn. The remaining cavity is filled with PMMA polymer (Garfin et al., 2001). Early clinical results have illustrated significant pain relief and reduction of morbidity, yet at the same time some potential complication issues of the procedure were also raised, including extrusion/leaking of the cement causing spinal cord injury, infection, hematoma formation, pulmonary embolus, failure to relieve pain, and fracture of adjacent vertebral bodies. A kyphotic deformity increases the anterior stresses in adjacent levels by changing biomechanical loads as they are transferred through the spine. Therefore, a vertebral fracture is a potential increased risk for subsequent fractures in adjacent vertebrae (Yuan et al., 2004).

Literature shows that vertebroplasty/kyphoplasty-derived subsequent adjacent fracture is a serious issue. Several studies were conducted to investigate the adjacent fractures after a kyphoplasty or vertebroplasty procedure. Uppin et al. (2003) reviewed 177 osteoporotic patients treated with vertebroplasty and found that 22 (12.4%) patients developed 36 new fractures, and 24 (67%) fractures occurred adjacent to the treated body.

Pflugmacher et al. (2006) reviewed 42 patients with 67 vertebral body fractures. In their 2-year follow-up after kyphoplasty, an adjacent fracture occurred in 8 (21.6%) patients with a total of 11 (18.3%) new adjacent vertebral body fractures.

Fribourg et al. (2004) treated 38 patients at 47 levels with balloon kyphoplasty. In the follow-up of 8 months, 10 patients had 17 subsequent fractures: 9 at above-adjacent levels, 4 at below-adjacent levels, and 4 at remote levels.

Harrop et al. (2004) treated 225 vertebrae in 115 patients with balloon kyphoplasty. A total of 26 patients developed 34 subsequent fractures at an average follow-up of 1 month. In this study, the incidence of subsequent fractures was 11.25% in patients with primary osteoporosis, while it was 48.6% in patients with secondary osteoporosis due to steroid therapy.

Hulme et al. (2006) reported from 12 reviewed studies on balloon kyphoplasty on fractures and found that 766 patients had 115 new fractures and of those 66% were located at an adjacent level.

Liu et al. (2015) conducted a long-term (5-year) follow-up study of OVCFs of 100 cases treated with either balloon kyphoplasty or vertebroplasty, wherein PMMA was used in both procedures as a bone filler. The authors concluded that an excessive angular correction was a critical concern in the risk of adjacent fracture after vertebroplasty, and only subtle differences were observed between vertebroplasty and kyphoplasty.

Kamano et al. (2011) investigated new vertebral compression fractures after prophylactic vertebroplasty (prophylactic cement injection for nonfractured vertebrae during percutaneous vertebroplasty for compression fractures) in osteoporotic patients. This retrospective study included 116 patients with osteoporotic compression fractures who underwent prophylactic percutaneous vertebroplasty. The results indicated that subsequent fractures in any vertebra occurred within 3 months after the procedure at 26 vertebrae in 21 patients (18.1%), and 36 occurred in 28 patients (24.1%) within 12 months.

Eichler et al. (2016) investigated the effect of prophylactic vertebroplasty of the adjacent vertebrae in single-segment osteoporotic vertebral body fractures treated with kyphoplasty. Patients treated with kyphoplasty for osteoporotic single-segment fractures between January 2007 and August 2012 were included in this retrospective study. The patients received either kyphoplasty alone (kyphoplasty group) or kyphoplasty with additional vertebroplasty of the adjacent segment (vertebroplasty group). The authors concluded that the prophylactic vertebroplasty of the adjacent vertebra in patients with single-segment osteoporotic fractures did not decrease the rate of adjacent fractures.

Kobayashi et al. (2009) performed prophylactic cement injection for 155 patients, with cement injected into the vertebra adjacent to the fractured vertebra, immediately above the fractured vertebra in the same procedure, and evaluated the frequency of new vertebral fractures and the efficacy of prophylactic therapy. The results indicated that fewer new fractures developed in the prophylactic group than in the non-prophylactic group at both 3 months and 1 year.

Jia et al. (2017) investigated the occurrence of new fractures in sandwich vertebra after cement augmentation procedures and evaluated the clinical outcomes after prophylactic vertebral reinforcement applied with resorbable bone cement. They analyzed 55 patients with at least one sandwich vertebrae and treated with percutaneous vertebroplasty. Eighteen patients were treated by prophylactic vertebroplasty with a resorbable bone cement to strengthen the sandwich vertebrae as the prevention group. The others were the non-prevention group. Their results showed that prophylactic vertebroplasty procedure could decrease the rate of new fractures of sandwich vertebrae.

From aforementioned data and discussion, it can be seen that, although kyphoplasty and vertebroplasty are generally considered safe procedures to treat OVCF, various complications may be derived from the procedures. One of the most frequent complications is the development of adjacent vertebrae fractures. It is interesting to note that neither Kamano et al. (2011) nor Eichler et al. (2016) concluded that a prophylactic cement injection into adjacent, nonfractured vertebrae during percutaneous vertebroplasty or kyphoplasty for OVCF could reduce the rate of adjacent fractures. On the other hand, Jia et al. (2017) and Kobayashi et al. (2009) concluded that the prophylactic treatment by cement injection into adjacent, nonfractured vertebrae could decrease the rate of new fractures of sandwich vertebrae. These "conclusions" are apparently mixed and inconclusive.

It is the present Inventors' belief that a truly prophylactic treatment to prevent OVCF must be an effective treatment to osteoporotic patients who has no history of vertebral fracture. In other words, the treatment must be conducted before the first vertebral fracture occurring to the patients.

SUMMARY OF THE INVENTION

The present invention is related to a minimally invasive method to prevent a potential fracture in an osteoporotic vertebra of an osteoporotic patient who has no history of vertebral fracture, which comprises first identifying an osteoporotic vertebra;

injecting a calcium-based cement paste into said osteoporotic vertebra, wherein the injected calcium-based cement paste will harden in said osteoporotic vertebra to form a hardened block, and at least a portion of the hardened block is bioresorbable and will be gradually replaced by a newly-grown bone structure in said osteoporotic vertebra.

Preferably, said injecting the calcium-based cement paste into said osteoporotic vertebra comprises drilling a hole on said osteoporotic vertebra, creating a cavity in said osteoporotic through said hole, inserting a distal end of a thin tube into said hole so that the cavity is fluidly communicated with a proximal end of said thin tube, and feeding said thin tube with said calcium-based cement paste from said proximal end thereof until a desired amount of said calcium-based cement paste leaves said distal end of the thin tube and enters said cavity.

Preferably, said injecting the calcium-based cement paste into said osteoporotic vertebra comprises drilling a hole on said osteoporotic vertebra, inserting a distal end of a thin tube into said hole so that an empty space in said osteoporotic vertebra is fluidly communicated with a proximal end of said thin tube, and feeding said thin tube with said calcium-based cement paste from said proximal end thereof until a desired amount of said calcium-based cement paste leaves said distal end of the thin tube and enters said empty space in said osteoporotic vertebra.

DETAILED DESCRIPTION OF THE INVENTION

Vertebroplasty (VP) and balloon kyphoplasty (BKP) are commonly used to treat vertebral fractures, especially osteoporotic vertebral compression fracture (OVCF) involving injecting PMMA into fracture-caused cavities. Due to the rigidity of PMMA causing mechanical incompatibility, the adjacent vertebral bodies have higher risks to subsequently fracture a few months after the surgery.

Injecting PMMA bone cement into adjacent osteoporotic vertebral bodies were tried to prevent them to continue to fracture, but the results are rather mixed and inconclusive. One major reason is believed due to the rigidity of PMMA.

It is the present Inventors' belief that a truly prophylactic treatment to prevent OVCF must be an effective treatment to osteoporotic patients who has no history of vertebral fracture, meaning that the treatment must be conducted before the first vertebral fracture ever occurring to the patients.

In the present invention, we propose to inject a more biocompatible, less rigid (than PMMA) and resorbable calcium-based bone substitute into an osteoporotic vertebra of an osteoporotic patient who has no history of vertebral fracture. To our knowledge, no one has tried this truly preventive method before.

PMMA has been used as a standard bone cement material in vertebroplasty/kyphoplasty procedures primarily due to its fast-developed strength which alleviates back pain and/or correct the deformity. Moreover, PMMA is able to be injected into the fractured vertebral body in vertebroplasty/kyphoplasty procedures, unlike calcium-based cement which will suffer a liquid-powder separation problem during the injection.

Compared to PMMA, calcium-based cement has many inherent advantages, such as its far better biocompatibility, osteoconductivity and resorbability (especially favorable to young patients), easily adjustable setting time, little or no heat release during setting, opaque to x-ray, etc. Despite all these advantages, the relatively low mechanical strength discourages its use for treating a primary vertebral body fracture without a proper mechanical stabilization/fixation treatment. Nevertheless, a non-dispersive, biocompatible and resorbable calcium-based cement can be an ideal candidate to treat a non-fractured, osteoporotic vertebral body using a percutaneous minimally-invasive procedure.

Another problem which must be overcome is that the two-phase fluid with high viscosity often makes a calcium-based cement paste difficult to be delivered via minimally invasive procedures. Without a proper cement formula or a proper minimally invasive delivery system, powder-liquid separation may occur leading to dispersion of the cement which may cause dangerous cement embolism.

A calcium-based cement suitable for use in the method of the present invention includes (but not limited to) the calcium-based cements disclosed in U.S. Pat. No. 8,784,551 B2; and U.S. Pat. No. 9,833,537 B2.

The all-synthetic, all-inorganic, highly osteoconductive and fully resorbable calcium phosphate/calcium sulfate composite cement disclosed in U.S. Pat. No. 8,784,551 B2 is featured by its non-dispersive behavior upon contact with blood/body fluid without need of polymeric or any other binder additive. The safety and efficacy of this product had been confirmed by a series of chemical/physical characterization and biocompatibility tests such as cytotoxicity, subchronic toxicity, intracutaneous reactivity, skin sensitization, genotoxicity and animal implantation with a series of different animal models including an osteoporotic goat spine model. The osteoporotic goat spine implantation study was conducted with a primary focus on histopathologic examination of the newly-grown bone structure in surgically-created bone voids in osteoporotic bony environment. The highly encouraging histopathologic examination indicated that this non-dispersive calcium-based cement formula, once implanted, can stimulate healthy, new bone to grow into the cavities and replace the cement implant even in a highly osteoporotic bony environment. With all these advantages, the present inventive method is not limited to use of this particular calcium-based formula. Any non-dispersive, minimally-invasively injectable biocompatible and resorbable calcium-based cement may be used in this inventive method.

To overcome the aforementioned powder-liquid separation problem, a minimally invasive cement delivery system such as those disclosed in U.S. Pat. No. 9,101,429 B2 can be used in percutaneous vertebroplasty (PVP)/vertebroplasty (VP). This unique multi-tunnel, plunger-less design of the delivery system solves the powder-liquid separation problem and can minimally-invasively deliver highly viscous cements effortlessly.

With all these advantages, the present inventive method is not limited to use of this particular minimally invasive cement delivery system. Any percutaneous minimally-invasive cement delivery system that does not cause powder-liquid separation may be used in this inventive method.

Practically in many cases the osteoporotic vertebra body is so porous that the calcium-based cement paste can be directly injected into the osteoporotic vertebral body without need to surgically create a cavity larger than a drilled hole diameter by a cutting tool such as the one disclosed in WO/2019/083784. For an osteoporotic vertebra that is not so porous, using the cutting tool to create a cavity before injection can be helpful.

REFERENCES

Batawil N, Sabig S, Metrics P X, "Hounsfield unit for the diagnosis of bone mineral density disease: A proof of concept study", Radiography 22, Issue 2, e93-e98, May 2016.

Chern Lin J H, Ju C P, "Bone cement formula and bioresorbable hardened bone cement composites prepared with the same", U.S. Pat. No. 8,784,551B2.

Dickman C A, Fessler R G, MacMillan M, Haid R W, "Transpedicular screw-rod fixation of the lumbar spine: operative technique and outcome in 104 cases", J Neurosurg 77, 860-70, 1992.

Eichler M C, Spross C, Ewers A, Mayer R, Külling F A, "Prophylactic adjacent-segment vertebroplasty following kyphoplasty for a single osteoporotic vertebral fracture and the risk of adjacent fractures: a retrospective study and clinical experience", J Neurosurg Spine 25 (4): 528-53, October 2016.

Fribourg D, Tang C, Sra P, Delamarter R, Bae H. "Incidence of subsequent vertebral fracture after kyphoplasty", J. Spine 29, 2270-6, 2004.

Garfin S R, Yuan H A, Reiley M A, "New technologies in spine: kyphoplasty and vertebroplasty for the treatment of painful osteoporotic compression fractures", Spine 26, 1511-5, 2001.

Han S, Wan S, Ning L, Tong Y, Zhang J, Fan S. "Percutaneous vertebroplasty versus balloon kyphoplasty for treatment of osteoporotic vertebral compression fracture: a meta-analysis of randomised and non-randomised controlled trials", Int Orthop 35(9), 1349-58, September 2011.

Harrop J S, Prpa B, Reinhardt M K, Lieberman I, "Primary and secondary osteoporosis' incidence of subsequent vertebral compression fractures after kyphoplasty", Spine 29, 2120-5, 2004.

Hulme P A, Krebs J, Ferguson S J, Berlemann U, "Vertebroplasty and kyphoplasty: a systematic review of 69 clinical studies", Spine 31(17):1983-2001, 2006.

Jia P, Tang H, Chen H, Bao L, Feng F, Yang H, Li J, "Prophylactic vertebroplasty procedure applied with a resorbable bone cement can decrease the fracture risk of sandwich vertebrae: long-term evaluation of clinical outcomes", Regen Biomater 4(1): 47-53, February 2017.

Ju C P, Chern Lin J H, "Method and apparatus for delivering cement paste into a bone cavity", U.S. Pat. Nos. 9,101,429, 9,445,855B2, 9,782,210B2.

Kamano H, Hiwatashi A, Kobayashi N, Fuwa S, Takahashi O, Saida Y, Honda H, Numaguchi Y, "New vertebral compression fractures after prophylactic vertebroplasty in osteoporotic patients", American Journal of Roentgenology 197, No. 2, 451-456, August 2011.

Kobayashi N, Numaguchi Y, Fuwa S, Uemura A, Matsusako M, Okajima Y, Ishiyama M, Takahashi O, "Prophylactic vertebroplasty: cement injection into vertebral bodies during percutaneous vertebroplasty", Acad Radiol. 16(2): 136-43, February 2009.

Liu J T, Li C S, Chang C S, Liao W J, "Long-term follow-up study of osteoporotic vertebral compression fracture treated using balloon kyphoplasty and vertebroplasty", J Neurosurg Spine 23(1): 94-8, July 2015.

Pflugmacher R, Schroeder R J, Klostermann C K, "Incidence of adjacent vertebral fractures in patients treated with balloon kyphoplasty: two years' prospective follow-up", Acta Radiologica 47:8, 830-840, 2006.

Uppin A A, Hirsch J A, Centenera L V et al., "Occurrence of new vertebral body fracture after percutaneous vertebroplasty in patients with osteoporosis", Radiology 226:119-24, 2003.

Yuan H A, Brown C W, Phillips F M, "Osteoporotic vertebral deformity: a biomechanical rationale for the clinical consequences and treatment of vertebral body compression fractures", J Spinal Disord Techn 17:236-42, 2004.

The invention claimed is:

1. A method for reducing a risk of a potential fracture in an osteoporotic vertebra of an osteoporotic patient comprising:

identifying an osteoporotic patient who has no history of vertebral fracture, and identifying a vertebra suffering osteoporosis, wherein said osteoporotic vertebra is diagnosed with a T-score lower than −2.5;

injecting a calcium-based cement paste into said osteoporotic vertebra, wherein the injected calcium-based cement paste will harden in said osteoporotic vertebra to form a hardened block, and at least a portion of the hardened block is bioresorbable and will be gradually replaced by a newly-grown bone structure in said osteoporotic vertebra, wherein said injecting said calcium-based cement paste into said osteoporotic vertebra comprises drilling a hole on said osteoporotic vertebra, followed by inserting a distal end of a thin tube into said hole so that an empty space created directly by said drilling in said osteoporotic vertebra is fluidly communicated with a proximal end of said thin tube, and feeding said thin tube with said calcium-based cement paste from said proximal end thereof until a desired amount of said calcium-based cement paste leaves said distal end of the thin tube and enters said empty space in said osteoporotic vertebra.

* * * * *